United States Patent
Claessens

(10) Patent No.: US 6,228,038 B1
(45) Date of Patent: May 8, 2001

(54) MEASURING AND PROCESSING DATA IN REACTION TO STIMULI

(75) Inventor: Dominique Paul Gerard Claessens, Geneva (CH)

(73) Assignee: Eyelight Research N.V., Willemstad (AN)

(*) Notice: Subject to any disclaimer, the term of this patent is extended or adjusted under 35 U.S.C. 154(b) by 0 days.

(21) Appl. No.: 09/155,594
(22) PCT Filed: Apr. 14, 1997
(86) PCT No.: PCT/NL97/00188
§ 371 Date: Sep. 30, 1998
§ 102(e) Date: Sep. 30, 1998
(87) PCT Pub. No.: WO97/38624
PCT Pub. Date: Oct. 23, 1997

(51) Int. Cl.[7] .................................................. A61B 5/00
(52) U.S. Cl. ............................ 600/558; 600/595; 351/210
(58) Field of Search ..................................... 600/587, 595, 600/558; 351/210

(56) References Cited

U.S. PATENT DOCUMENTS

| | | | |
|---|---|---|---|
| 4,815,839 | * 3/1989 | Waldorf | 351/210 |
| 4,885,687 | * 12/1989 | Carey | 364/413.02 |
| 4,894,777 | * 1/1990 | Negishi et al. | 364/419 |
| 4,988,183 | * 1/1991 | Kasahara et al. | 351/210 |
| 5,137,345 | * 8/1992 | Waldorf et al. | 351/206 |
| 5,204,203 | * 4/1993 | Hutchinson et al. | 351/210 |
| 5,555,895 | * 9/1996 | Ulmer et al. | 600/595 |

* cited by examiner

*Primary Examiner*—Cary O'Connor
*Assistant Examiner*—Pamela L. Wingood
(74) *Attorney, Agent, or Firm*—Foley & Lardner

(57) ABSTRACT

Method and device for collecting and processing stimuli data and measuring the reactions to them, in which the physiological reactions of respondents to the stimuli presented, or components thereof, are measured automatically and are recorded in one or more computer systems. Recorded data, stimuli data, whether or not in combination with respondent data, are automatically processed, e.g. in central units, to interpretable results which, stored in a database, a relational database for example, are accessible to anyone under certain conditions.

29 Claims, 3 Drawing Sheets

MEASURING AND PROCESSING DATA IN REACTION TO STIMULI

BACKGROUND OF THE INVENTION

The invention relates to a method and device for collecting and processing stimuli data and measuring the reactions to said data.

Such a method is known from U.S. Pat. No. 5,226,177. With this method, the object is to find out how a number of respondents react to e.g. advertisement illustrations and slogans, tv and cinema commercials, images of persons, logos and other things presented to them. With the known method, one can employ, among other things, answering through push buttons. This can lead to deviations and measuring errors, e.g. by incorrect operation of the push buttons, which can be the cause of incorrect final results. Such errors in final results can also be caused by the fact that respondents feel hindered to give their true opinions, and give an opinion best suitable to the buttons.

SUMMARY OF THE INVENTION

Therefore, the object of the invention is to provide an improved method, by which in a short time, e.g. within one day, a measurement with one hundred or more respondents and with several hundreds of stimuli can be executed, said measurement being applicable in several places, also on an international scale, simultaneously or otherwise. According to the invention, such a method is characterized in that the physiological reactions by respondents to the stimuli presented, or to components of said stimuli, are measured automatically and are recorded in one or more computer systems and that the recorded data, stimuli data, combined with respondent data or otherwise, are automatically processed, e.g. in central units, to interpretable results, said results stored in a database, e.g. a relational database, being accessible to anyone on certain conditions.

The invention relates to a method, as well as a device for massively collecting, processing and making available stimuli performance data and random check survey data within a short time, by massively presenting stimuli to large amounts of respondents, and measuring and recording physiological reactions to said stimuli.

The stimuli concern e.g. visual stimuli, including printed matter, products, illustrations, photos, texts, instructions, manuals, etc., in printed media, including magazines, newspapers, specialist journals, brochures, flyers, free local papers, DM, books, guides, etc. But also stimuli such as e.g. TV-stimuli, productions, spots and/or packages, shop formulas, design, art, concepts, apparatus, models (e.g. car models), reality and photo product concepts, as well as presentation by e.g. projection on screens, including TV-screens.

With the method according to the invention, it is possible to perform qualitative research on a quantitative scale. It unites the high degree of reliability of the quantitative research with the great variety in subjects and depth of the qualitative research.

The device to be used with the method according to the invention comprises a combination of apparatus and subsystems organizationally enabling measurement of the reactions of e.g. more than one hundred persons a day to e.g. several hundreds of stimuli. With the data obtained by said apparatus, for the first time it is possible to produce accurate calculations as regards to qualitative information. At the same time, for the first time it is possible to mutually compare results of calculations and thereby obtaining judgments and insights.

The possibility of confronting e.g. more than one hundred respondents to several hundreds of stimuli in the same way on one day, recording both the visual and other physiological reactions to said stimuli, processing said reactions to clear measurement reports and making said reports available for interested persons within a few hours, in any case within one day, is a breakthrough in relation to all existing methods, applied technologies and devices.

Persons interested in the measurement reports are e.g. companies advertising, marketing officials, design, film and television production, product development, media proprietors, etc. Persons can take an interest in the stimuli data, to the random test data and/or to the data concerning the reactions of the random test on the stimuli presented.

For example, with the use of advertising in marketing activities, everything is about the effectivity thereof. It is of the utmost importance, to find out to what extent an advertisement message is absorbed, and if so, how this can be maximised. Here, the detailed data of the measurement reports play an important role. A lot of information becomes available to the commercials designers, by which e.g. shortcomings can be removed.

For example, just like with the known method, the stimuli can be presented on screens, e.g. television screens. Presenting the stimuli to the respondent can take place by means of a computer-controlled program for reproducing on displays stationary or moving images, combined with sound or otherwise, in which the program is adjusted according to items and for the purpose of presenting stimuli in certain sequences, dependent on demographic data and/or the recorded physiological reactions of a respondent during the measurement.

Here, the computer systems provide for coordination between the presentation, the recording and the adjustment of the presentation program employing a common time base.

However, other than with the known method, with the method according to the invention, particularly the presentation of the stimuli to the respondents can also take place in the form of printed media, e.g. magazines and/or newspapers. This way of presentation corresponds to the natural situation. In that situation, the computer systems provide for recording and identification of the stimuli, the presentation thereof occurring as a consequence of the opening of the pages by the respondent. At the same time, the computer systems provide for time and duration recording per presented pages (identified by the computers).

One of the important physiological reactions concerns the direction of the centre of the eye. Therein, it is typical, that as the respondent is allowed more natural freedom, the accurate measurement values are more difficult to obtain.

In order to be able to determine the position a respondent focusses the centre of his eye on, other methods apply a number of different procedures. The method mentioned earlier is characterized by a data recording unit which is positioned on the head of a respondent (headset or "glasses") and is secured by means of a clamping band. Here, the condition is that the "glasses" can maintain an unchanged position in relation to the head.

As regard to the images, the output of these "glasses" is approximately in adjustment, but movement of the glasses cannot be prevented. Also, weariness and resistance generally occur within 10 minutes. The output is mostly just one videotape with the measurement data of one or some respondents, whose images should be processed and interpreted mainly frame by frame. Furthermore, the results can be affected.

The known eye movement recording systems operate on the basis of fixed references. The stimulus is fixed to the sensor, or the glasses have been fixed on the head, or the head is fixed in relation to the sensor, in any case, there are always geographical references.

With the method and the system according to the invention, no fixed reference is applied. Instead, a clock time, e.g. atomic clock, is applied for all moving parts. All parts, including the respondent's head, the eyes, the radiation sources, the reflections at the cornea, the mirrors, the sensors, the arrangement and the stimuli, are allowed to move in relation to each other within the room. Per unit of time, all moving parts are brought into synchronization adjustment in relation to each other (adjustment: a preselected arrangement of the parts). Time is the fixed reference, without geographical reference. In this way, a fully natural freedom for the respondents is realized for the first time. The head can freely move within wide limits. There is no fastening of parts to the head and the natural freedom of head movement, e.g. sitting on a chair, is not hindered or even affected. In order to be able to realize this, among other things, the positions of the head, the eyes, the pupils, the pupil centres, the reflections at the cornea, the position of the eyes in the eye sockets, as well as the position of the stimuli in relation to the eyes, are synchronously determined at every instant of measurement. To that end, the device is provided with accurate sensors for being able to find the positions in time and follow them and for being able to use this information for bringing the parts in adjustment, with the result, that the head and the stimulus can move freely and yet the eye position on the stimulus can be determined accurately. This method can be applied both in its entirety and partly.

The method according to the invention is fully automated. Physiological reactions of respondents, such as eye activity, including movements of the eye, viewing direction, pupil size, blinking frequency, position, orientation and movements of the head, eye-stimulus distance, as well as changes thereof in time, etc., are measured in real time, digitized, recorded and are subsequently, without manual functions or personal intervention, processed to results on-line. Due to this, respondents, operators and/or third parties basically don't have the opportunity to influence the results of the measurements.

When compiling the program to be performed, one can already bear the person in mind, e.g. preferences and/or interests of the respondent. Variables such as sex, age, demographical data and social situation are preferably recorded for each respondent individually.

Further, according to the invention it can be provided for, that preceding the presentation of the interactively selected stimuli or otherwise, the absorbing capacity, the tempo, the reading ability, the respondent's interest for product categories, and/or all other conceivable personal characteristics, are determined and that by way of those, through printed matter or e.g. through models in 3D, the program on the screen is adjusted to the respondent concerned. To that end, the determined personal characteristics can e.g. be recorded through a chip card. By way of the data on the chip card, e.g. the program items can be compiled.

Like with the known method, there is the possibility of carrying out a survey in a number of places or locations at a distance from each other. An extension of the method provides for the possibility of putting together the measurement data of a number of individual systems, geographically separated or otherwise, in a central processing unit and processing them to results as a whole.

By measuring certain physiological reactions of respondents, it is possible to not only measure the reaction to one stimulus in its entirety, but also the reaction to certain components thereof.

Apart from the physiological reactions already mentioned, furthermore, according to the invention one or more of the following or other physiological reactions of respondents can be measured and recorded:

physiognomy, such as the positions of the corners of the mouth, of the eyebrows, the tensions on the facial muscles, etc.;

blood pressure;

heartbeat;

breathing;

muscle tensions;

skin temperature;

skin resistance;

brain waves;

blood flow throug a part of the body, such as e.g. the earlobe, etc.;

hand movements;

the voice;

etc.

On finding some of these last-mentioned reactions, contrary to the reactions mentioned earlier, one can particularly act in such a way, that sensors, electrodes or other means to be fixed to the body might have to be employed. Also, it might be that certain measured reactions can only relate to the overall impression of stimuli shown.

With measuring eye activities, one can operate particularly in such a way, that one or two eyes are radiated at with invisible or unnoticable reflecting radiation and recordings are made with one or more recording elements connected to one or more computer systems, e.g. position sensors, eye and pupil detection sensors, other sensors or cameras. by which e.g. at the same time the eye convergence process can be recorded. Here, radiation can be of a continuous nature but e.g. intermittent too, e.g. adjusted to the measuring instants of the sensors. The radiation can originate from optical radiation sources, such as those of visible light, IR and UV optical radiation, but also from all conceivable sources of radiation of another type, such as those of ultrasound, radar and X-ray.

One can also act in such a way, that for exposure or recording, optical elements are employed, mirrors having certain transmission and reflection properties, for example. Larger mirrors and application of several image-following sensors enables all occurring head movements e.g. suitable with a sitting posture, to be tolerated without loss of an accurate indication about what the centre(s) of the eye(s) is/are focussed on. Owing to this, at the same time, the admissible dimensions of the stimuli become virtually unlimited and the accurate indication will also be maintained if larger stimuli are presented, moving and/or rotating or otherwise. With extensive stimuli, such as parts of shops, such as shop shelves, for example, we no longer speak of presentation.

For measuring the eye viewing direction, e.g. by means of a moving source of radiation, the eyes can be radiated at and the place and orientation of the pupils can be determined. Furthermore, the movement of the pupil, or its centre also when they are partly covered, can be measured in relation to the image of the radiation source at the cornea. From the relative positions of the radiation source images in relation to one or two pupils in the recorded images, the eye viewing direction can be determined.

When using radiation or light sources, dark pupils in relation to illuminated irises are achieved. When using radiation or light sources being positioned coaxially in relation to the camera, pupils brightly illuminated in weakly illuminated surroundings are achieved. Both possibilities and variations thereof, and other possibilities can be used as desired, separately as well as combined.

The eye viewing direction, position of the head, and viewing position in a plane, can only be determined accurately if the eyes, the pupils, the sensors, the exposures and possibly other, optical or not, components are brought in very accurate adjustment to each other in time, or, continuously or not, are kept in adjustment to each other. The system according to the invention provides this necessity by means of dynamic calibrations, measuring the posture and position of head, pupils, eyes with light reflections and stimulus and spatial following thereof. In order to realize this, a number of known and other means are applied, both separately and in combination.

The measurements of position, orientation and movements of the head, as well as the distance between head, eyes and stimuli, and the changes therein in time, provide less detailed, yet not less important information about the reactions of respondents to presented stimuli. For example, having a stimuli identification and positioning system record how the process of persons reading, leafing through magazines, newspapers or other printed matter, such as DM, goes. Such as: which pages were opened, for how long did the respondent look to the left, the right, the bottom and the top? When looking carefully at stimuli, including the above, but also other stimuli such as packages etc., one often tends to bend forward. A reduction of the distance between head and stimulus can go together with giving attention. The reverse also holds good: An increase of the distance between head and stimulus can go together with slackening of attention. These examples show that in this way, a large amount of information about the behaviour with objects and printed matter can be obtained without the application of eye movement registration.

For the sake of determining individual facial features, and the ability to correct them, a calibration can be provided, e.g. by asking respondents to look a certain locations in a plane. It has appeared, that on looking under orders to certain locations in a plane, the eye is able to take up an angular position, which e.g. can result in deviations that can have the size of a circle having a diameter of some tenths of millimetres, e.g. 50 mm, taken across the usual viewing or readinq distance, which is so inaccurate, that therefore, the subsequent measurements get indications of fixation locations that can be situated at a distance of +50 mm or –50 mm from the actual fixed object. According to the invention, one acts in such a way, that for determining the calibration, one uses locations with figures consisting of a number of characters being different per group, e.g. dots or rectangles, the number of which should be counted aloud by the respondent. One can only count with the fovea part of the eye. Since the respondent, in order to be able to count, must aim the fovea centralis accurately, a careful calibration can be performed while he is counting. Here, it should be observed, that the retinal part of the eye is always used, whereas it doesn't require an exact position of fixation. It can observe many things simultaneously, but none of it accurately. It is misleading for use with calibration purposes: while looking at one of the outer letters of FIG. 1, one can also see the other two. However, in order to be able to count the number of points in the circles behind the letters of FIG. 1, the fovea centralis must be aimed at them. Counting aloud indicates the moment at which this happens.

For presenting the stimuli, the system is equipped with one or more stimuli presentation units, e.g. displays, including video screens, one or more reading tables and/or other stimuli presentation means. A reading table could be provided with lighting and/or a clamping device for positioning and fixing printed media. For clamping printed media, a number of known methods and other methods can be employed, both individually and combined.

For measurement and registration of the reactions to the presented stimuli, the systeem is e.g. equipped with one or more measuring members and/or recording elements, e.g. sensors, including cameras; buttons, including push buttons, with interactive reaction or otherwise; members for touch screen answers; and/or other or further measuring members e.g. for measurement and registration of blood pressure, brain waves, etc.

According to the invention, the system for application with the method described above will comprise central computers e.g. being in communication with a number of substantially identical measurement and registration devices arranged at spaced apart locations, each device consisting of computer units and measuring members connected to said computer units, for measuring the physiological reactions of the respondents to the presented stimuli. The computer units and the central computers dispose of a common time base, or of relatable or synchronizable time bases, as a consequence of which all measurement results of each period and each location can be compared and combined. Due to that, the measurements of each of the measurement units performed in interval of time can be cumulated legally, which is necessary for a random check n=100, in which e.g. 3 papers are measured in 6 hours.

The raw data of the measurements comprise, among other things, the respondent reactions and the stimuli data coupled to them by means of the time axis. From one or more locally arranged devices, the raw data are transmitted to the central processing units such as main computers, and are subsequently processed to data e.g. per measurement, per stimulus, per stimulus item and per respondent. The resulting data are stored in a database, e.g. a relational database, e.g. per measurement, per stimulus, per stimulus item and per respondent. It is is also possible to store references to the data in the database, instead of storing the actual data. The references indicate where the actual data are stored and can be found. This method is particularly preferred in case of large files and/or a fast increase in volume of the files.

In addition, among other things, additional data are collected, classified and stored in the database. Advertisements are e.g. stored in classes. Classes concern e.g.: in which media the advertisements were placed, the release dates, page numbers, dimensions and use of colours. Yet also the positions in advertisements, indicated by means of boxes, polygons, contours and/or other shapes, where the advertisement elements are situated, such as: the logo, the products, the texts, the headlines, etc.

For example, sex and age of respondents are stored. But also the demographic data, education and social data. Furthermore, the personal interests and the physical and psychological capacities, including sight, reading and absorbing capacities, spectacle corrections as well as the tempo of absorption and processing, etc.

Through dialogue units, the database is accessible, at a distance and under certain conditions or otherwise, and the database can be 'interrogated' about everything conceivable which is related to, or might be related to, the data stored in the database and, per subject, combinations of data. By means of software programs, the results of that can be specified into information providing insight, that can be presented as measurement reports.

The measurement reports can contain information about one of the stimuli presented to respondents, or about a selected number of stimuli. The reports contain e.g. information about publicity of certain brands; about certain activities; about advertisements placed in certain media, or about certain product categories. The measurement reports can also concern data of the random check survey, or subgroups thereof. For example, the reactions to stimuli by men, women, or men over 30, etc. Further, the measurement reports can concern any conceivable combination of data.

BRIEF DESCRIPTION OF THE DRAWINGS

The invention is further explained by way of drawings, FIGS. 1 to 3, in which flow charts are shown as examples, for explanation and as examples of the method according to the invention.

DETAILED DESCRIPTION

Figure 2:
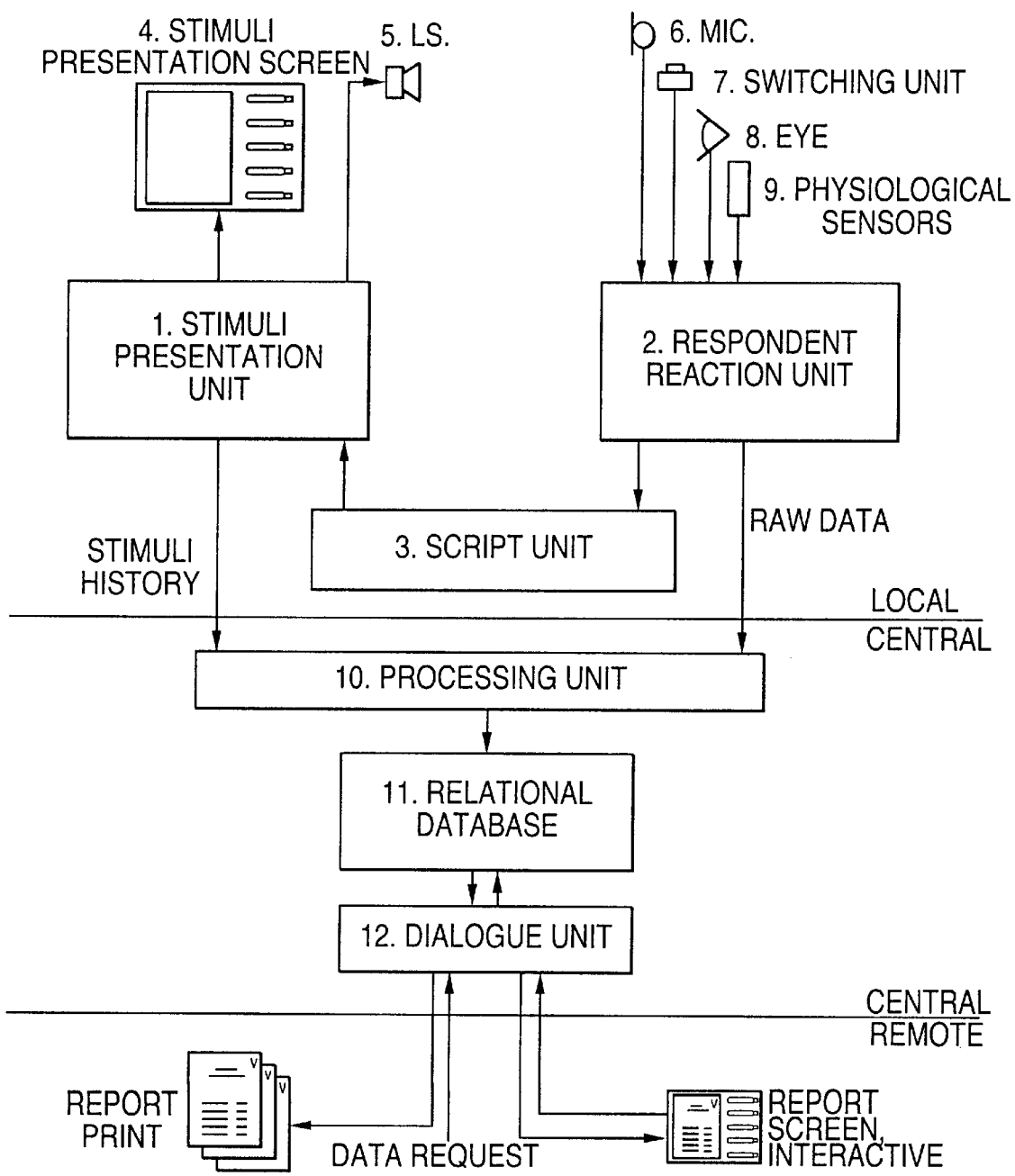

As shown in FIG. 2, a stimuli presentation unit 1 and a respondent reaction unit 2 are controlled by a script unit, or script generator 3. On the one hand, the script unit provides for presentation of the stimuli and on the other for coordination of the measured reactions of the respondent to those, and, subsequently, for interactive adjustment of the further progress of the script.

The stimuli are presented on a screen 4. In connection with the respondent's ability to ask questions about the stimuli shown and his ability to answer, the screen can be equipped with facilities for those purposes, e.g. window and/of touch screen facilities. Audio stimuli, including acoustic signals, but e.g. also questions and/of assignments, are reproduced through a signal giver, a loudspeaker 5, for example.

The respondent reaction unit receives, measures and registers a respondent's reactions, consisting of voice reactions through microphone 6, pressure or touch reactions through push button, touch screen or all other conceivable means by which respondents can express their reactions 7, eye reactions symbolically indicated by eye 8, and physiological reactions by means of physiological sensors 9.

The reactions to stimuli presentation interactively affect e.g. the script unit 3, so that adjustments to the further progress of the script during a program are always possible.

From one or more locally arranged devices, the raw data of a measurement, obtained from the respondent reaction unit, as well as the "stimuli history", that is, the stimuli program shown e.g. under interactive action, are sent further to central processing units 10, such as main computers, so that said raw data can be processed to data e.g. per stimulus and per respondent. Said data are stored in a database 11. By means of one or more dialogue units 12, the relational database, at a distance and under certain conditions or otherwise, are 'interrogated" about everything conceivable which is related to, or might be related to, the data stored in the database and, per subject, combinations of data. By means of software programs, the results of that can be specified into information providing insight, that can be presented on screens or in the form of printed reports.

Figure 3:
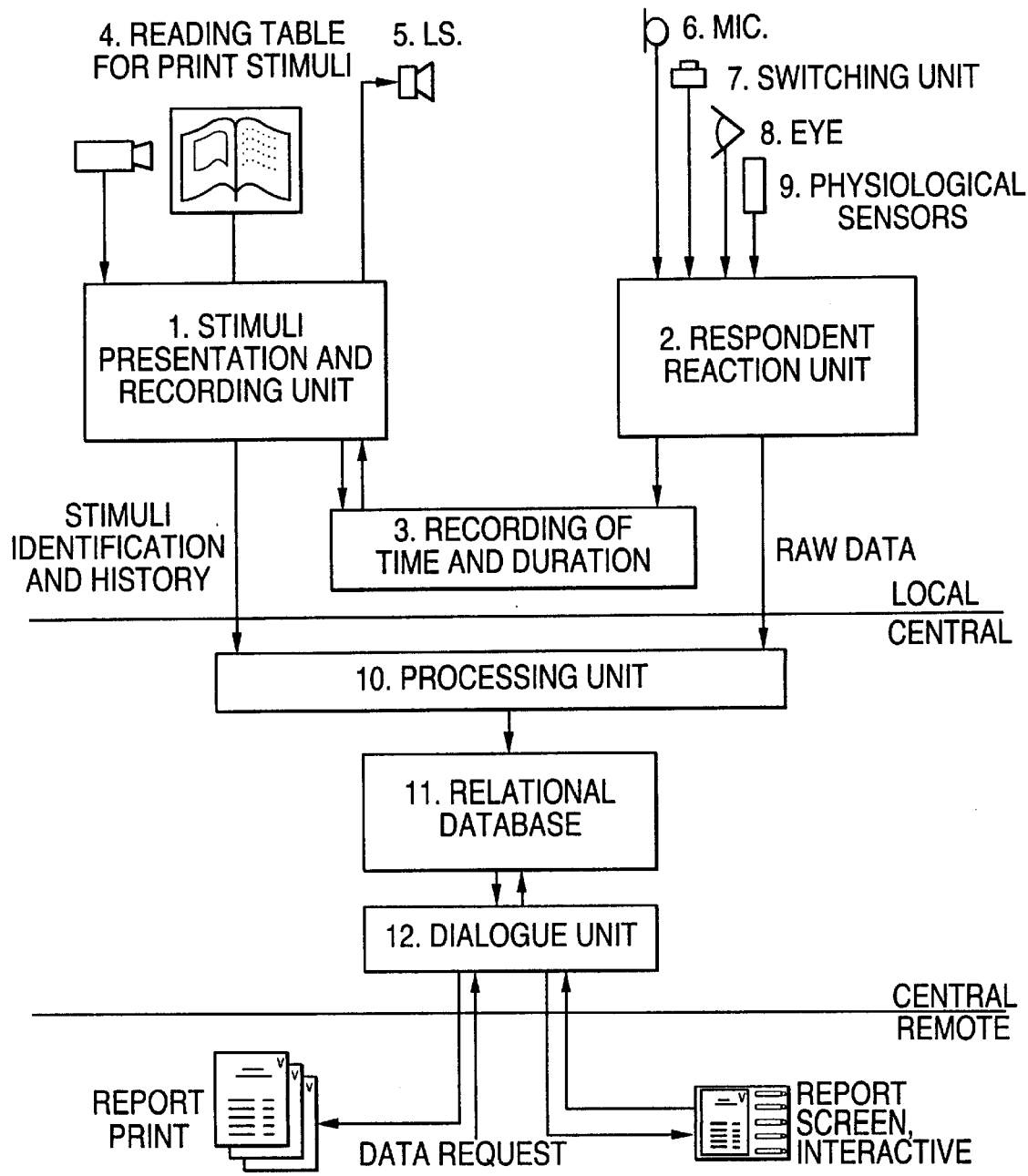

FIG. 3 shows, as an example of another embodiment of the method according to the invention, a flow diagram in which printed stimuli are presented, positioned on one or more reading tables. The stimuli presentation and registration unit comprises one or more reading tables on which the print stimuli, e.g. in the form of magazines and papers, are positioned, and fixed or otherwise. For example, by opening or not opening the pages, respondents choose the stimuli themselves. All stimuli presented by opening the pages are registered and, contrary to other methods, automatically identified. To that end, the system consists of one or more sensors by which characteristics of stimuli can be registered and processed and are kept available for comparison. The system works both on the identification of a stimulus in its entirety and on partly invisible stimuli, including stimuli largely covered. For example, a partly opened magazine or paper will already be sufficient to be able to determine the number of that page with certainty. Rotations up to 180° are tolerated. The processing is fast, yet not always real time, which is not always necessary. There are a number of known and other identification methods, which can be employed, in combination or otherwise, for identifying stimuli.

Furthermore, with the method according to the invention it is possible to determine the position and/or orientation and/or distortion of the stimulus per measuring instance and, either simultaneously or later, compensating for them. Distortion of stimuli can be the consequence of e.g. magazine or paper pages bulging. In this way, it is possible to register manipulations of and with stimuli by respondents, such as with printed matter the way of holding and/or moving pages. Yet also manipulation of objects, e.g. turning objects for the purpose of looking at them in several views. Preferably, the measuring situation is such, that during the instances of recording, the stimuli are not or only slightly moving.

With application of the method according to the invention, the data relating to the head posture, head position, position of the eyes, eye position in the eye sockets, pupil position and viewing direction will be related to above-mentioned stimuli data. Owing to that, for the first time it is possible to determine, dynamically and for each measuring instance, which stimuli, and which parts thereof, are visible, which part thereof is actually in the respondent's visual range, and, in particular, to accurately determine for each instance on what stimulus part the centre of the eye, the fovea centralis, of the respondent is focussing.

In other words, the position and orientation of the stimuli in relation to the position and orientation of the head together with the "visual field" of the respondent and the visibility of the stimuli parts. The position and orientation of the stimuli in relation to the positions and orientations of the eyes together with the visibility of the stimuli parts provide the parts of the stimuli which will be depicted on the "fovea centralis". All "determinations" of all parts concerned should be made for each measuring instance in such a way, that the information can be used for ringing said parts in register.

In addition to registration and identification of the stimuli, the starting time and the length of time are determined, during which e.g. pages of magazines are lying open and thus stimuli can be visible. Depending on the possible exceeding of a, e.g. preset, maximum length of time to be spent per stimulus, per page, per double page or per magazine, a signal as a reminder can be given through a signal giver, e.g. a loudspeaker 5.

The method according to the invention also provides for identification of the behaviour characteristic of reading. Depending on the possible exceeding of a, e.g. preset, maximum length of time to be spent reading, including e.g. reading headlines of advertisements or editorial texts in magazines, likewise, a reminder can be given through the signal.

For the rest, the flow according to FIG. 3 corresponds to the one described with FIG. 2.

By way of example, step by step a method will be described, which can be followed together with the process and system according to the invention for determining the position on a stimulus on which the centre of the eye of a respondent is focussed.

1. Determining the presence of the head by means of a multiple sensor device composed of one or more, e.g. image producing, sensors, including e.g. one or more cameras.

2. Determining the 3-dimensional position and orientation of the head, e.g. with the help of the device as described at 1.

3. Determining the most likely position of the eyes in the head, of the centre of the eye and the point of reflection on the cornea, e.g. with the help of the device as described at 1.

4. Controlling the geometrical range of one or more eye detection sensors, such as e.g. adjusting the image field of one or more image forming sensors, such as cameras, by one or more motor drives, to the position of the eyes and subsequently setting the sensors in relation to the eye distance, such as focussing when using depicting optics, followed by checking the set geometrical range and, if necessary, correcting and adjusting them. Preferably, the eye detection sensors are separate sensors being able to operate parallel to, coupled to, but e.g. also more or less indenpendent of, the sensors described at 1. For irradiation of the eyes, the eye detection sensor can be equipped with one or more radiation sources preferably having invisible beams of rays. By coupling the sources to the sensors mechanically, for example, the geometrical range of the assembly can be controlled synchronously. The advantage thereof is, among other things, that there is directional irradiation and that a higher radiation intensity on the eyes is achieved with less energy and that relatively small radiating angles of the sources suffice for achieving a large spatial range.

5. Determining that the eyes are within reach of the eye detection sensors.

6. Determination of the momentary characteristics of eyes, eyelids, corneas and pupils, such as e.g. the degree to which the eyelids are open, or to what extent the corneas or the pupils are covered by the eyelids; the pupil sizes and the contrasts between iris and pupil.

7. Determination of the transitions between pupil and iris.

8. Reconstructing the transition curves between pupil and iris, determining the degree of roundness of the pupils and, e.g. in case of elliptical shape, caused by natural distortion or perspective, for example, determination of the ellipse axes and the spatial orientations and positions of said axes. These reconstructions and determinations serve, among other things, for being able to accurately determine the pupil centre, despite a perspective distortion as a consequence of the sensor-pupil geometry.

9. Determination of the pupil centre.

10. Determination of the centre of the positions of the reflections of the radiation sources on the corneas, e.g. by generating histogram distributions of e.g. the radiation intensities of the reflections in different directions.

11. Determination of the distortions of e.g. an image of said reflections in relation to the spatial profiles of the emission sources as a consequence of characteristics of the eyes, including aqueous humour and/or the eye distances in relation to the eye detection sensors.

12. Calculating the viewing directions in the room.

13. Correcting the calculated viewing directions with the previously measured individual parameters of the eyes, including e.g. shift, scale and similar and other (non-) linear corrections.

14. Correcting the spatial eye positions determined at 3.

15. Correcting the geometry and/or optics of the arrangement.

16. Bringing the multiple corrected viewing directions in register with the 3-dimensional position and orientation of the positioning planes, such as tabletops of reading tables, of the stimuli to be presented.

17. Calculating the fixation positions on the positioning planes of the stimuli to be presented.

18. Measurement and calculation of the 3-dimensional orientation, position and situation of a presented stimulus, e.g. a printed stimulus, including e.g. a page of a magazine or paper, or an object, in relation to the positioning planes.

19. Coupling the fixation location of the eyes on the positioning planes to the presented stimulus.

20. Correction of the calculated fixation locations, of the eyes on the presented stimuli, for the measured and calculated 3-dimensional orientation, position and situation of the stimulus.

All steps are performed such, that a net time resolution of at least $\frac{1}{50}$ of a second and a location resolution (on the stimuli) of at least 1 mm$^2$ are realized.

By way of an example, it is indicated step by step which aspects, among others, can be measured with the system and method according to the invention. The aspects concern items of typical printed matter research.

1. A diagnosis of respondents, e.g. itemized in:
    sex,
    age,
    education,
    demographic variables,
    social variables,
    areas of interest,
    preferences, e.g. in relation to brands and products,
    which magazines are read,
    habits, e.g. smoking and drinking,
    visual, auditive and psychological capacities,
        absorbing capacity,
        reading capacity,
        understanding capacity,
    tempo,
    calibration, etc.
2. A diagnosis of stimuli, e.g. print media, itemized in:
    number and type of magazines,
    number of pages,
    number of pages opened and the page numbers,
    number of pages respondents left opened for more than X seconds, and page numbers,
    pages on which respondents placed more than X fixations, and page numbers,
    number of fixations per page, per quadrant page, or smaller, e.g. $\frac{1}{8}$ of a page.
    time spent for a complete magazine, per page, per quadrant page, or smaller, e.g. $\frac{1}{8}$ of a page, etc.
    Above diagnoses itemized seperately for:
        advertisement pages,
        editorial pages,
        left pages, right pages,
front and back pages, etc.
3. The aspects of stimuli, such as:
orientation in medium: date, issue, page number, location, subject, theme,
size,
style, colour use, etc.
Performance aspects:
   The degree to which stimuli, e.g. advertisements, are capable of realizing an observation by respondents,
   To what extent all parts of an advertisement regarded as necessary by the advertiser are fixed by respondents,
   The number of persons that fixated one, two, or three of the three central advertisement elements,
   The degree to which stimuli, e.g. advertisements, are (in)capable of establishing contact with respondents.
   Ad contact,
      e.g. defined as: the percentage of respondents who placed at least one or more fixations on the ad according to certain time criteria.
      Ad contact means the start of taking in the stimulus.
   No ad contact,
      e.g. defined as: the percentage of respondents who did not open the double page, on which the ad was placed, or did not place any fixations on the advertisement according to certain time criteria.
   The performance aspects following below are related to whether or not fixating one or more of the three central advertisement elements.
   The three central advertisement elements (C.A.E.) are:
      Brand in parts
      Visual in parts
      Text in parts
Partial Advertisement Contact (PAC)
   e.g. defined as: the percentage of respondents having fixated the brand + the two other central advertisement elements, each with individual time criteria, e.g. between 60 and 1000 ms.
   Partial Advertisement Contact is a requirement for the capability to take note of a part of the brand message, in such a way that absorption thereof becomes possible.
Complete Advertisement Contact (CAC)
   e.g. defined as: the percentage of respondents having fixated the brand + the two other central advertisement elements, each with individual time criteria, e.g. between 60 and 1000 ms.
   Complete Advertisement Contact is a necessary requirement for the capability to fully absorb, process and store the advertisement information.
The Advertisement Contact Score (ACS)
   e.g. defined as: the result of Partial and Complete together.
   The Advertisement Contact Score percentage indicates the number of respondents who could have absorbed the stimulus in such a way, that at least a correct, be it a partial one, recall is possible.
   The criteria to be employed, e.g. the ACS criteria, are preferably adjustable. Thus, a difference in requirements can be employed e.g. for known stimuli in relation to unknown stimuli.
All data are relative in relation to:
   other stimuli.
   the same stimulus in other media.
   the same stimulus at other times.
4. The circumstances during the measurement, such as:
   date and moment of the day.
   the moment of measurement, e.g. separation of morning, afternoon and evening results.
   the total number of respondents,
   the total number of magazines and/or papers,
   the total number of pages,
   the total number of advertisements,
   the news situation (including topical matters and sports), etc.
   the social-economical situation,
   the temperature (indoors and outdoors),
   the atmospheric humidity level and atmospheric pressure,
5. Any conceivable combination of 1, 2, 3 and 4.
   It will be obvious that in the above, the invention has only been explained by way of some specific examples, as for the method, the equipment used with it, the applications and the possible result of measurements, and that many changes and/or additions can be made without leaving the inventive idea.

What is claimed is:

1. A method of collecting and processing stimuli data and random check survey data and presenting stimuli to respondents, comprising the steps of:
   presenting said stimuli to respondents,
   measuring and recording the physiological reactions to said presented stimuli with several systems, said respondents, said stimuli, and components of said systems moving in relation to each other and being brought into spatial synchronization with each other per unit time, regardless of dimensions and movements of said respondents, said stimuli, and said components of said systems,
   presenting said stimuli in large quantities,
   processing said data to interpretable results, and
   storing said processed data in a searchable database.

2. The method according to claim 1, wherein the measurements are performed at a number of spaced apart locations and the recorded data are processed in central units.

3. The method according to claim 1, wherein clock times are applied instead of fixed geographical references, said time being the fixed reference for measurements, calculations and processing.

4. The method according to claim 1, wherein the physiological reactions occur in at least one of the respondent's head, the respondent's eyes, and the reflections at the respondent's cornea, and said components of said systems include at least one of radiation sources, mirrors and sensors.

5. The method according to claim 1, wherein data concerning 3-dimensional position, orientation and movements of a respondent's head, a distance between a respondent's head, eyes and stimuli, and changes therein in time are related to the stimuli data, so that dynamically and for each measuring instance the method determines which stimuli are visible to what extent and which parts thereof are actually within a visual range of the respondents.

6. The method according to claim 1, wherein data concerning a position of a respondent's head, a position of a respondent's eyes, reflections at a respondent's cornea, a position of a respondent's pupil and viewing direction are related to the stimuli data so that dynamically and for each measuring instance the method determines on what stimulus element the eye center of a respondent is focused.

7. The method according to claim 1, wherein the interpretable results realized by data processing concern stimuli performance aspects and respondent performance aspects.

8. The method according to claim 1, wherein the measuring and recording steps are accomplished by at least one of sensors for measuring physiological data, radiation sources, push buttons, interactive push buttons, touch screens, interactive touch screens and signal givers.

9. The method according to claim 1, wherein the step of presenting said stimuli in large quantities is accomplished by means of computer-controlled programs for showing still and moving images on displays in combination with sound, in which the programs present stimuli in a certain sequence, depending on conditions.

10. The method according to claim 9, wherein the programs adapt depending on the physiological reactions of the respondents.

11. The method according to claim 9, wherein the programs adapt depending on stored personal data.

12. The method according to claim 11, wherein computer systems provide for coordination between presentations, recordings and adaptations of presentation programs, employing relatable time bases.

13. The method according to claim 12, wherein the relatable time bases comprise synchronizable time bases.

14. The method according to claim 12, wherein the relatable time bases comprise a common time basis.

15. The method according to claim 9, wherein, during stimuli presentation programs, each time after certain time intervals, an adjustment to the respondent is checked and possible deviations are automatically corrected.

16. The method according to claim 1, wherein the step of presenting stimuli to respondents is accomplished by presenting stimuli in the form of at least one of printed matter, products in 3-D, and designs.

17. The method according to claim 16, further comprising, prior to the step of presenting stimuli to respondents, positioning the stimuli on a table.

18. The method according to claim 16, further comprising, prior to the step of presenting stimuli to respondents, fixing the stimuli in a fixed position.

19. The method according to claim 16, further comprising determining 3-dimensional positions and rotations of the stimuli per unit of time and using the 3-dimensional positions and rotations for spatial synchronization of elements of the measurement arrangement.

20. The method according to claim 16, further comprising determining spatial orientation and shape of the stimuli per unit of time and using the 3-dimensional positions and rotations for spatial synchronization of elements of the measurement arrangement and for correction.

21. The method according to claim 16, further comprising the steps of recording and identifying presented stimuli by means of computer-controlled sensor systems.

22. The method according to claim 1, wherein information about 3-dimensional position, orientation and movements of a respondent's head and about a distance between the respondent's head and stimuli, and changes therein in time, are determined per unit of time.

23. The method according to claim 1, wherein information about 3-dimensional position, orientation and movements of a respondent's head, a distance between a respondent's head, eyes and stimuli, positions of a respondent's eyes, positions of a respondent's eyes in the eye sockets, positions of a respondent's pupils and reflections at a respondent's cornea, and changes therein in time are determined per unit time, and the information is used for spatial synchronization of elements of the measurement arrangement.

24. The method according to claim 1, further comprising the steps of measuring eye activity, such that at least one eye is irradiated with directional radiation by means of moving radiation sources, and recording the eve activity with recording elements that are connected to the systems.

25. The method according to claim 24, wherein movement of pupils and their centers is measured with regard to each measuring instance in relation to images of radiation sources on a cornea, and viewing directions of an eye are determined from the relative positions of the images in relation to the pupils.

26. The method according to claim 1, wherein the physiological reactions of respondents are measured and recorded per unit of time, the physiological reactions comprising at least one of the physiognomy, blood pressure, heartbeat, respiration, muscular tensions, skin temperature, skin resistance, brainwaves, blood flow through a part of the body, hand movements, and the voice.

27. The method according to claim 1, wherein measuring the physiological reactions includes measuring and correcting individual facial features of respondents by measuring a direction of fixation of eyes in relation to certain directions of calibration.

28. The method according to claim 27, wherein determining the directions of calibration is accomplished by employing locations consisting of a group of small characters varying per location, said characters together being no larger than several mm's, varying in number per location, which number is counted aloud by respondents, so that respondents aim their fovea centralis accurately on the groups of characters to make calibration possible.

29. The method according to claim 1, further comprising determining a stimuli program to be executed, recording personal data including at least one of variables, capacities, characteristics, preferences, interests and interests in product categories and brands, and tuning the stimuli program to be executed to said data and to the recorded physical and psychological capacities of respondents including at least one of absorbing capacity, tempo and reading capacity.

* * * * *